United States Patent [19]

Smit

[11] 4,134,405
[45] Jan. 16, 1979

[54] CATHETER AND INTESTINE TUBE AND METHOD OF USING THE SAME

[76] Inventor: Julie A. Smit, 1045 Hinman Ave., Evanston, Ill. 60202

[21] Appl. No.: 757,929

[22] Filed: Jan. 10, 1977

[51] Int. Cl.² ............................................. A61B 17/00
[52] U.S. Cl. ...................................... 128/303 R; 3/1; 128/348
[58] Field of Search ......... 128/DIG. 9, 303 R, 350 R, 128/349 R, 348, 132 R, 1 R; 3/1

[56] References Cited

U.S. PATENT DOCUMENTS

| | | | |
|---|---|---|---|
| 2,230,218 | 2/1941 | Asche | 128/349 R X |
| 2,492,384 | 12/1949 | Kaslow | 128/350 R UX |
| 3,333,588 | 8/1967 | Schulte | 128/350 R |
| 3,395,710 | 8/1968 | Stratton et al. | 128/350 R |
| 3,521,620 | 7/1970 | Cook | 128/303 R X |
| 3,625,200 | 12/1971 | Muller | 128/348 X |
| 3,834,394 | 9/1974 | Hunter et al. | 128/325 |

*Primary Examiner*—Robert W. Michell
*Assistant Examiner*—Michael H. Thaler
*Attorney, Agent, or Firm*—Charles A. Laff; J. Warren Whitesel; Howard B. Rockman

[57] ABSTRACT

A first part of the inventive instrument comprises an insertion and removal device in the form of a catheter which may be inserted through the mouth, pharynx, and esophagus into the stomach. The catheter includes an outer sheath which protects the human body while a tool extending coaxially through an inner sheath is being manipulated. The tool includes a remotely operated pair of tweezers for holding or releasing a loop on insertion or seizing and holding the loop on removal of the second part of the inventive instrument. The second part of the instrument comprises a tube for implantation in the small intestine. While it is so implanted, the tube prevents food from being there absorbed by the body. The tube may be used to treat obesity or alcoholism, or to cover an ulcer and give it an opportunity to heal without exposure to digesting food.

22 Claims, 10 Drawing Figures

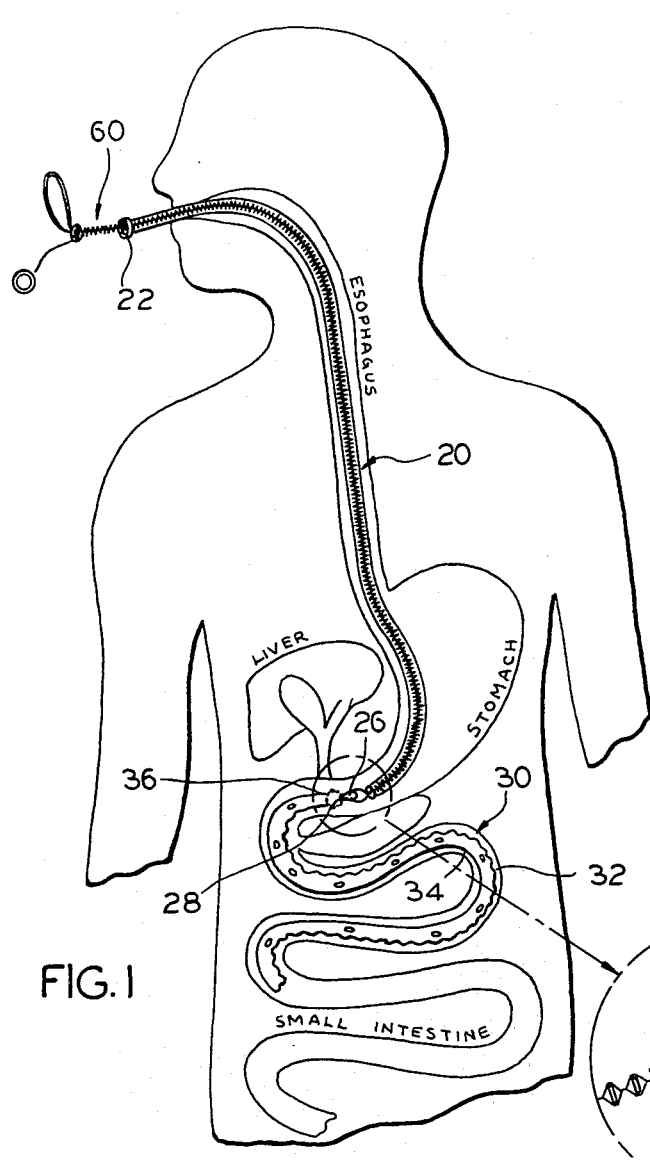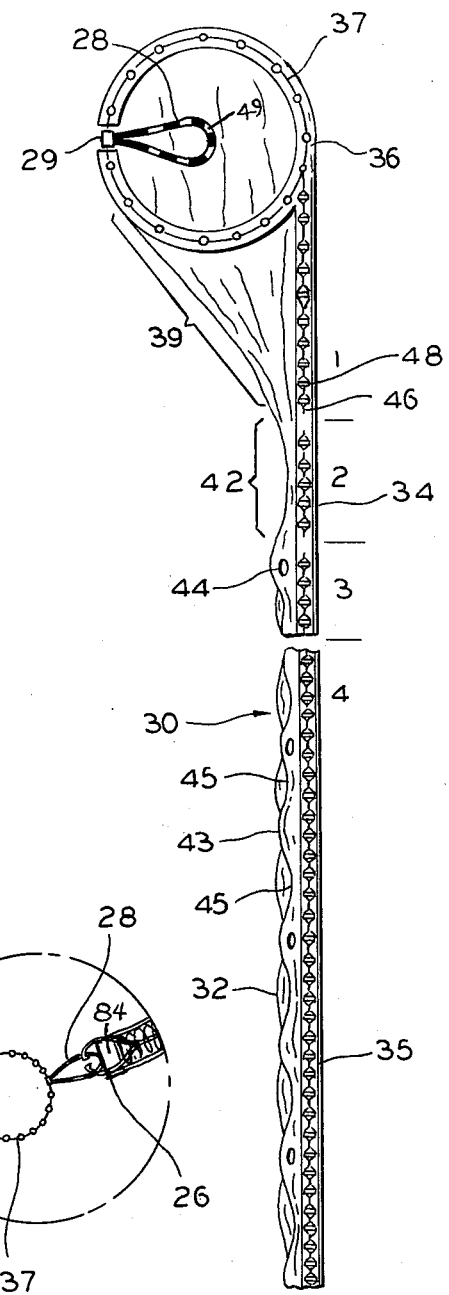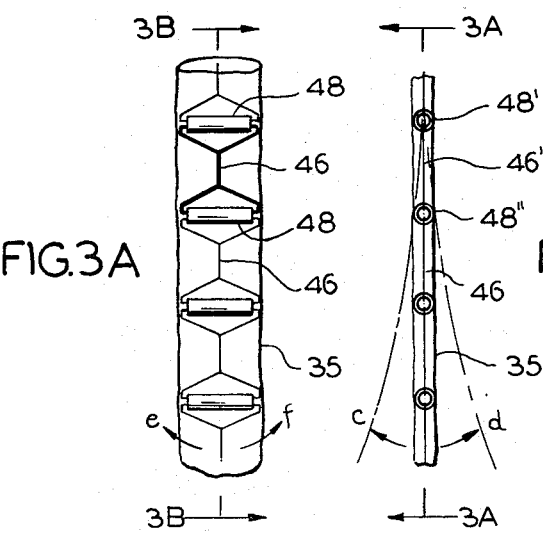
FIG. 1
FIG. 2
FIG. 3A
FIG. 3B

U.S. Patent   Jan. 16, 1979   Sheet 2 of 2   4,134,405
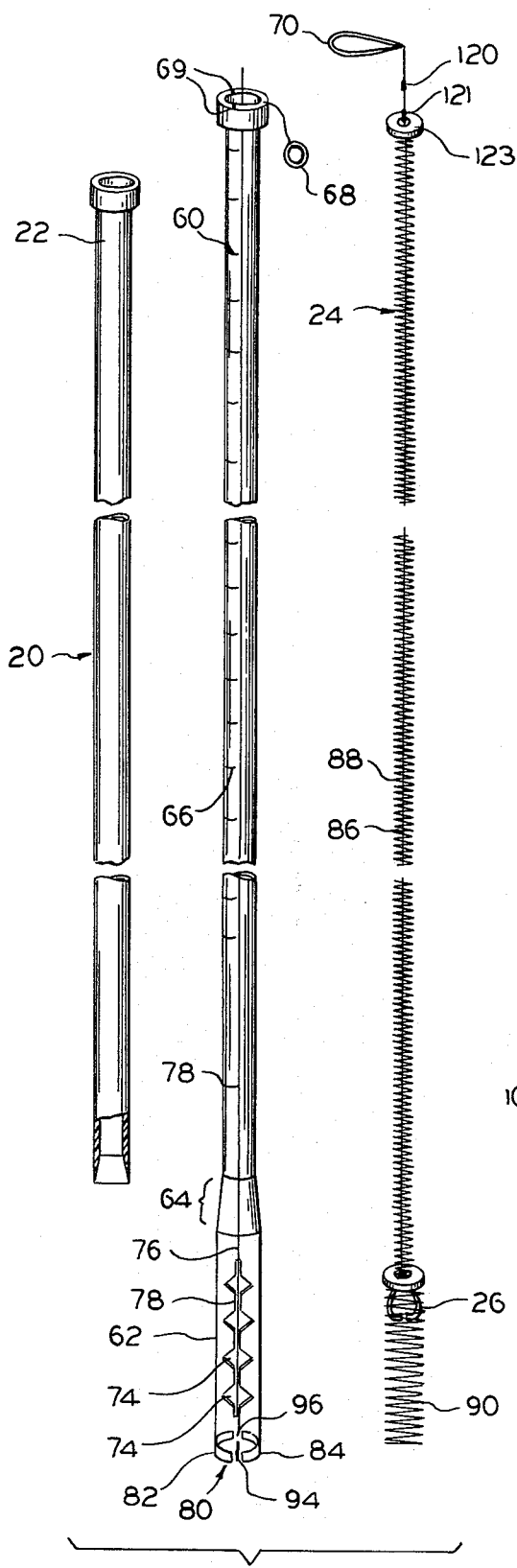
FIG. 4
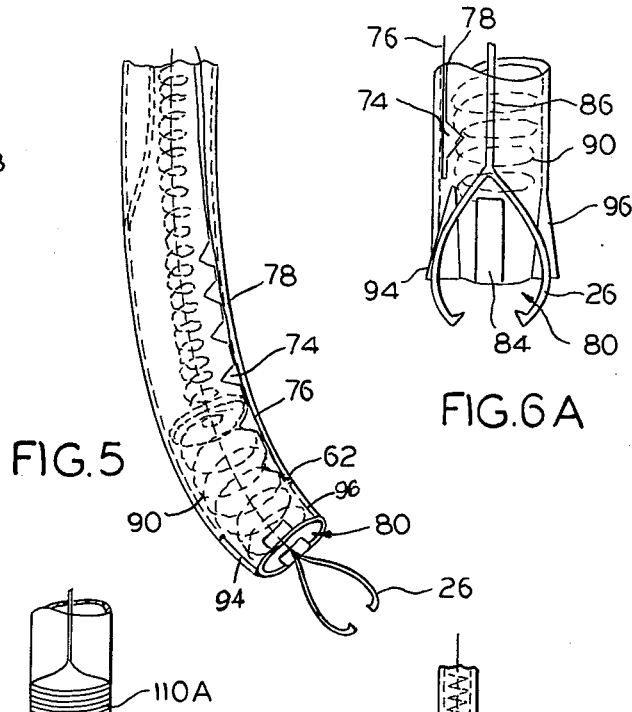
FIG. 5
FIG. 6A
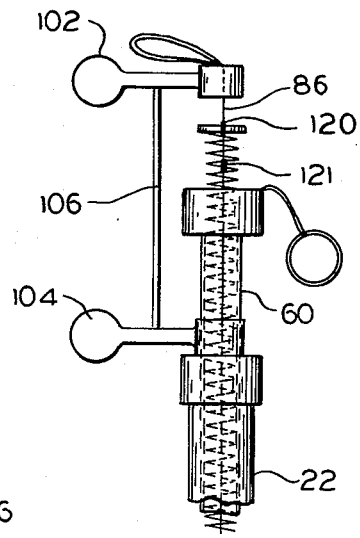
FIG. 6B
FIG. 8
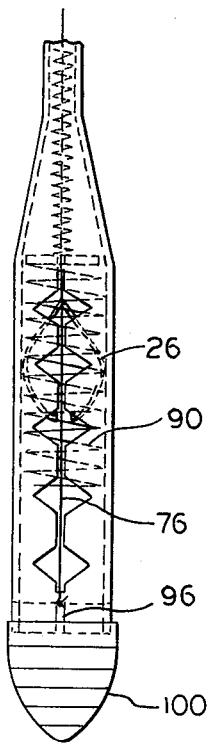
FIG. 7

CATHETER AND INTESTINE TUBE AND METHOD OF USING THE SAME

This invention relates to medical appliances more particularly to devices for lining body passages, especially—although not exclusively—to devices for lining portions of the human alimentary canal.

There are many times when it may be desirable to provide a tube for lining a passage in a human or animal body in order to control, prevent, restrict or even accelerate a transfer of chemicals through the walls of the passage. Exemplary of such a lining is a tube extending through portions of the small intestine in order to prevent or restrain digesting food from there being absorbed by the body. This lining may be used to restrict absorption and thereby serve as a treatment for obesity, alcoholism, ulcers, or the like. The lining may also be perforated to enable a high level of chemical transfer. The implant would stimulate the villi causing an increased absorption of food chemicals necessary for weight gain or for treating absorption-related deficiencies.

In greater detail there are two basic types of peristaltic movements. One type pushes the food along while the other type concentrates on squeezing the food into the villi for absorption. This weight gain idea is based upon the concentrated peristaltic movements essential for food absorption. An implant would stimulate the villi causing the squeezing process to last longer in a given section of the intestine before moving the food on to the next section. The intestinal walls will squeeze longer if something is present whether it be food or a tube. Therefore, increased absorption takes place. This principle is substantiated by experiments reported by Meyer O. Cantor in his book *Intestinal Intubation*. The embodiment of this invention could be altered in several ways to increase absorption. One way is perforating the lining to enable a high level of chemical transfer.

Consider the particular problems of obesity, by way of example. Some people are unable to lose weight under any normal procedures. Therefore, in the past they have submitted to surgical treatment wherein portions of the intestine have been either cut out or by-passed to reduce the absorption area of the intestine. However, there have been undesirable side effects when such surgical treatment is used. For example, these side effects have included uncontrollable diarrhea, electrolyte imbalance, unpredictable weight loss, reflex of nutritious chyme proximal to the site of anastomsis, and failures in the anticipated degree of bypass. Thus, there is a need for a less drastic method of reducing the absorption area of the intestine, without resorting to surgery.

Accordingly, an object of the invention is to control the effective area of a passageway in an animal body. Here, an object is to control the absorption surface area of the human alimentary canal, without having to resort to irreversible procedures, such as surgery or dangerous drugs such as amphetamines. In particular, an object is to cover a large part of the absorption area of the intestines in order to reduce or alter absorption by means of a reversible procedure which may be undone if unwanted side effects persist.

Another object of the invention is to cover an ulcerated portion of the intestine so that it may have time to heal without being exposed to the digestive process.

Still another object of the invention is to cover a portion of the intestinal absorption area for treatment of obesity.

A further object is to delay passage of food through the intestine in order to increase absorption.

Yet another object of the invention is to accomplish these and other objects without affecting normal body processes such as peristaltic contraction, glandular secretions and the like. Here, an object is to accomplish these objects in a manner which may be reversed if unwanted side effects should interfere with such normal body processes.

In keeping with an aspect of the invention, these and other objects are accomplished by a two part instrument. The first part of the instrument is an insertion and removal device in the form of a catheter which may be inserted through the mouth, pharynx, and esophagus into the stomach. The catheter includes an outer sheath which protects the body from irritation while manipulating an inner sheath which contains a tool. The tool includes a remotely operated pair of tweezers for holding or releasing a loop on insertion or seizing and holding the loop on removal of the second part of the instrument.

The second part of the instrument is an extremely thin wall tube containing a semi-flexible chain and terminating in a retaining ring having the loop attached hereto. The chain is rigid in one direction to enable the tube to be pushed into the alimentary canal without danger of the tube twisting, while the chain remains completely flexible in a perpendicular direction so that it may curl around to follow the intestinal path. The tube itself has a very thin wall so that it does not interfere with normal peristaltic contractions. Yet, the tube walls are also impervious so that food will not be absorbed through the intestine wall.

The nature of a preferred embodiment may be understood best from a study of the attached drawings, wherein:

FIG. 1 is a schematic diagram showing the inventive tube implanted in the small intestine, and the catheter in a position where it is about to be used to remove the implant;

FIG. 2 schematically shows, somewhat in perspective, a long thin tube which may be implanted in a small intestine;

FIG. 3 shows in two views (in two perpendicular planes), the flat, semi-flexible chain having two flexure modes encased in a support tube, FIG. 3A being taken along line 3A—3A of FIG. 3B and FIG. 3B is taken along line 3B—3B of FIG. 3A;

FIG. 4 is a perspective view of each of the three main parts of the catheter which is used as a tool for implanting and removing the tube of FIG. 2;

FIG. 5 shows the device at the end of the catheter for controlling the degree of curl in the lower section of the catheter as it is used for insertion and removal of the implant;

FIG. 6A pictorially shows how tweezers are oriented and extended from the inner tube of the catheter;

FIG. 6B shows an alternative capture means in the form of an electromagnet;

FIG. 7 shows, by way of example, the inventive catheter, after it has been prepared for insertion into the stomach preparatory to the retrieval of the implanted tube and FIG. 8 shows a safety guard which may be used to secure the parts of the catheter in place during insertion and removal of the implant in FIG. 2.

In the description which follows, any suitable medical grade of plastic, or other material may be used. At present, it is thought that a silicone material should be used, such as "Silastic", for example. "Silastic" is a registered trademark for Dow Corning's silicone elastomer materials, and related products. Information on this material is contained in Bulletin: 51-247, date: September 1975, which is available from the Medical Products Business Division of Dow Corning Corporation, Midland, Michigan 48640.

According to this bulletin, "Silastic" is a clear, seamless material designed for use in a variety of clinical and laboratory applications. The material is easy to clean and is specifically suited for surgical drains, suction equipment and catheter applications, and general hospital applications which demand inertness, non-reactivity, stability to heat and aging, and non-reaction to body tissue and fluid. It contains no plasticizers or additives to leach out, and it will not support bacterial growth. It has a soft pliability which contributes to a significant reduction in tissue irritation normally associated with long-term catheterization. It resists fatigue with repeated flexing or stretching. It is a nonwetting silicone elastomer with a surface that minimizes blood platelet destruction and contact hemolysis resists clotting, sticking, and incrustation, and assuring an excellent flow characteristic. Regardless of whether "Silastic" material is or is not used, the material should have these characteristics.

This or other material is used to make the inventive two-part instrument. The first part 20 of the instrument is a catheter which is used as an insertion or removal device or tool which may be inserted through the mouth, pharynx, and esophogus into the stomach. The catheter 20 includes an outer sheath 22 which protects the esophagus and other body parts from abrasion or irritation while the tool 24 is being manipulated inside the inner sheath 60. The tool includes a remotely operated pair of tweezers 26 for holding or releasing a loop 28 on insertion or removal of the second part 30 of the instrument, which is a tube 32.

The second part 30 (FIG. 2) of the instrument includes a long and extremely thin wall tube 32 containing a semi-flexible, flat chain 34. Tube 32 is designed to be implanted in the intestine to cover the villi, and to cut or alter the absorption of food, calories, alcohol, or the like.

The combination of the catheter and tube 32 with a gelatin capsule 100a on end 40 is pushed down the throat and into the stomach of the patient. Current medical treatment includes an employment of catheters which are so forced into the intestine in this manner. Therefore, the intestinal tube 32 may be worked into the intestine in a known manner. Since the wall of tube 32 is very thin, the tube does not interfere with normal peristaltic contractions while it is implanted in the intestine. Yet, the tube wall is also strong enough not to rupture, and it is also impervious so that food is not absorbed through the portion of the intestine wall which is lined by the tube. Both the tube 32 and chain 34 terminate at one end in a retaining stomach ring with a loop 28 attached to ring 36 by means of a tiny turnable tube 29 (i.e., tube 29 rotates about the axis of the ring 36 circumference). This stomach ring is exemplary of various methods of securing the tube in place and the pylorus is exemplary of various locations for holding the ring in place. For example, on more permanent implants involving an operation, the tube could be stitched in place. The other end of the tube is open. The chain 34 has a non-flexible mode which enables the tube 32 to be pushed into the alimentary canal without danger of twisting. The chain 34 also has a flexible mode so that it may curl and follow the natural intestine path.

The stomach ring 36 expands under the resilience of the silicone encasing a section 37 of the flat chain. The chain section 37 is rigid in the direction in which it would have to collapse, in order to pass out of the stomach and into the intestine. Therefore, it implants itself against the stomach walls to anchor the end position of the tube 32. To hold the tube 32 in place, the ring 36 fits snugly in the pyloric portion of the stomach. Preferably this anchoring occurs solely because the ring 36 is too large to pass through the sphincter muscle which opens wide enough to pass about an object which is one cubic centimeter.

The walls of the ring 36 are contours on a basis of the ease by which food may enter the intestine. Attached to the back of the ring 36 is the thin-walled tube, which begins with a funnel shape 39. Then, there is a portion 42 having a reduced diameter, which goes through the pylorus and thereafter opens to approximately the diameter of the small intestine. The tube curves through the small intestine, following the normal intestine path. The walls of the tube are pierced periodically by oval holes, one of which is seen at 44. These oval holes 44 are preferably about ¼ inch long × ⅛ inch wide. They are punched through the tube walls so that the patient receives a controlled amount of nutrition and so that the food inside the tube receives intestinal digestive juices. If very few, widely spaced holes are provided, there is little absorption. If a great number of closely spaced holes are provided, the passage of food may be delayed to increase the absorption from a given amount of food. This way, the food leaving the tube will be in approximately the normal state of digestion, for that part of the intestine—only the amount of absorption is changed. More preferably, it is thought that absorption may be controlled for adjusting weight gain if ring 36 is used alone with chain 34 and its encasement 35. Tube 32 is removed leaving ring 36 to hold chain 34 and its encasement 35 in place to stimulate absorption.

The number of the holes and the length of the tube may vary widely, depending upon the desired medical effects. Preferably, the length of the tube is in the range of ½ foot to 4½ feet. The stomach ring 36 and funnel-shaped tube section 39 begin about 1⅛ inch diameter and narrow to about ⅝ inch. The tube diameter remains at approximately ⅝ inch for about 1½ inches–2 inches in region 42, which is a length that is sufficient to fully pass through the pylorus and to accommodate any shifting or pulling which may occur responsive to the peristaltic waves of the stomach and intestine.

After section 42, and continuing for the remaining length of the tube, its walls are molded to billow and constrict as seen at 43, 45, respectively, and be shaped somewhat as the interior of the intestine is shaped. The important point is not to fit the billows exactly into matching folds in the intestine, but is that the amount and distribution of material in the tube walls should approximately match the amount and distribution of material in the intestine so that the tube may seat and fit itself into the intestine with little or no stretching or bunching.

The billowing begins about 3¾ inches from the stomach ring 36 (well beyond the pylorus) and continues for the length of the tube. Preferably, any suitable number, such as approximately 4–8 lengthwise accordion folds are molded along the entire length of the tube with the number of folds depending upon the width to be reduced. These folds reduce the width of the tube body to approximately ⅛ inch, which dimension is maintained unless the tube is filled with food. Food is squeezed into and through the tube 32 by the normal peristaltic waves in the stomach and intestine. As a result, the food causes the longitudinal folds in the tube to open, and the compressed walls of the tube bulge outwardly. The intestinal walls feel this bulge and the normal peristaltic wave motion results. Thus, unless tube 32 is distended by food, it is in a compressed form.

The balloon-thin, walls of tube 32 are kept stable and prevented from twisting by means of the semi-flexible, flat chain 34 which is enclosed and secured inside of both tube 32 and ring 36. Preferably, the flat chain 34 is slightly wider than the inside diameter of its encasement, tube 35, when in its originally manufactured condition. The encasement, tube 35, keeps the chain 34 from bunching up and in a somewhat straight path unless tube 32 is positioned around a curve in which case chain 34 bends with its encasement, tube 35, to correspond with the curve. The chain 34, its encasement, tube 35, and tube 32 are the same length. Preferably the chain and its encasement run along one side and are glued or embedded in the tube wall.

The "semi-flexible" is used herein to mean a device (such as a chain in FIG. 3) is made so that it is able to move or flex in only one plane. It cannot move or flex appreciably in any other plane, especially one which is perpendicular to the flexible plane. In greater detail, one exemplary chain (FIG. 3) is made from a plurality of links fashioned from rigid rods, wires, or plastic sections 46. Each link may be thought of as two "Y" members with their stems integrally attached together (for ease of identification, one of the sections is outlined in heavily inked lines in FIG. 3A). The arms on each end of each "Y" embrace and somewhat loosely fit into a tubular member, as at 48. Thus, for example, each of the links 46 may swing freely within its associated tubes 48 with motion in directions c, d (FIG. 3B). This means that the chain is almost completely flexible in directions c, d. On the other hand, there is very little give in a plane (FIG. 3A) which are taken at right angles to the flexible plane. The arms of the "Y" prevent movement in directions e, f. In its insertion condition, the tube 35 is transversely stretched slightly by the chain 34, thereby giving a greater stability in the non-flexible directions e, f. Thus, the tube 32 is prevented from twisting and bunching, and it is rigid when manipulated in directions e, f, while it is almost completely flexible when manipulated in directions c, d, yet retains a straightened path from its encasement.

The ring 36 is silicone enclosing the semiflexible chain ring 37 that fits snugly into the pyloric portion of the stomach. While the ring 36 is large and strong enough in the non-flexible dimension of the chain 37 so that it does not pass the sphincter, it is sufficiently flexible in another dimension to be compressed within the catheter during insertion and removal. The shape of the retaining ring is such that it moves with and adapts to the stomach's contour. The top and the bottom walls of the ring 36 are preferably thicker than the side walls so that the ring prefers to be squeezed up and down but not from side to side.

The loop 28 hangs about halfway into the lumen of ring 36. This loop 28 has a magnetic property. In greater detail, the loop 28 may be a silicone tube approximately 0.025 inches in diameter and 1 inch long. Tiny segments of magnetically attracted material, such as a magnetic plastic material or steel are enclosed within the tube. Preferably, this magnetic material is opaque to X-rays so that it may be recognizable under a fluoroscope. The two ends of the loop are attached to the turnable tube 29 which fits somewhat loosely around a straight section in the chain 37 embedded in the ring 36, so that the loop (and therefore ring 36) may be captured and deflected from its normal position responsive to a magnetically attracted material on the end of the catheter. When a connection is made between the magnets 82, 84 and the loop 28, the free end of loop 28 is drawn into and enters the catheter, the ring 36 is also drawn in and compressed behind the loop for insertion into and removal from the body. Therefore, it is preferable for the chain 37 and the loop 28 to have an even number of uniformly spaced links 46 or magnetic segments 49, respectively, so that, upon compression, there is a precise fold with each link being aligned with a corresponding link on the opposite side of the ring or loop.

The catheter 20 of FIG. 4 is used when the tube 32 is inserted or implanted in the small intestine, and when it is later removed therefrom. A knowledgeable doctor may be able to insert and remove the implant without the use of a fluoroscope, because the magnets perform the tweezer and loop alignment function without requiring precise human guidance. In general, this catheter 20 comprises three coaxial, tubular members, which are separately shown in FIG. 4. The outside tubular member is sheath 22. The intermediate tubular member is inner tube 60. The inner-most tubular member is the tool 24. The sheath 22 and inner tube 60 are telescopingly fitted together to vary the effective length of the catheter in order to conform to a patient's stature. In effect, the sheath 22 functions as a lining for the mouth, pharynx, and esophagus so that the tool running through it may be manipulated without directly rubbing or irritating these and similar body parts.

In greater detail, the inner tube 60 is a longer and thinner diameter tube, which fits inside the shorter and slightly wider diameter sheath 22. The inner tube 60 may be about 28 inches long, including a handle portion. The sheath 22 may be about 22⅝ inches long, including a handle. The outside diameter of the inner tube 60 should be about 2 mm less than the inside diameter of the sheath 22 for maneuverability. The preferred measurements for these parts are approximately:

| Inner Tube 60 | Sheath 22 |
| --- | --- |
| 4 mm I.D. | 7 mm I.D. |
| 5 mm O.D. | 9 mm O.D. |

Approximately, the bottom four inches 62 of the inner tube 60 widens to become an outside diameter of approximately 7 to 9 mm, which is the same as the outside diameter of sheath 22. Therefore the two tubes appear to the digestive tract as one continuous catheter of substantially the same outside diameter.

The considerations for these measurements are that the inner tube 60 should have the smallest inside diameter that may contain a workable tool 24 or an alternate means as seen as an electromagnet in FIG. 6B. The walls of the inner tube should be about ½ mm thick, for currently available materials. The taper 64 of the widening portion 62 of the inner tube 60 should occur within about one inch of catheter length. This one inch length is selected since it is long enough for a gradual change and not too long to interfere with the performance of the tool. The bottom three inches 62 of inner tube 60 must have an inside diameter which is large enough to receive the loop 28 and compressed stomach ring 36. Also, the walls of section 62 must be strong enough to withstand the pressure caused by this compression of ring 36.

The length of inner tube 60 is marked at 66 in centimeters or inches, starting about 10 inches from the bottom of the catheter and ascending to the top so that the total usable length of the catheter is easily known when parts 22, 60 are telescoped together. Preferably, these numbers are upside down on one side, relative to the numbers on the other side, so that the telescoped length may be easily read, regardless of the catheter's position when read.

A pair of handles 68, 70 are associated with the inner tube 60 for manipulating the catheter. In greater detail, the lower and enlarged end 62 of the inner tube 60, has a series of semi-circumferential wedge or V-slots 74 (FIG. 5) cut therein perpendicular to the axis of the tube and covered with a thin layer of silicone or other desirable material. A cord 76 runs down a passageway 78 in the tube wall, extending almost the entire length of the inner tube 60. The cord passageway 78 ends about ⅛-¼ of an inch from end 80 of the inner tube, before slit 96 begins. The cord 76 extends loosely through notches 74 and is attached to the lower end of the inner tube 60 at to the passageway through which cord 76 passes. Therefore, when the cord 76 is pulled, by means of an extending handle 68, the V-notches tend to close, thereby curling the inner tube over a radius which is variable, depending upon the tension in cord 76. This curling enables the end 80 of the inner tube to be pointed in a particular direction. Hence, by pulling the cord a discrete distance and by rotating the inner tube 60, within sheath 20, the end 80 may be guided through the stomach and toward the pyloric portion of the stomach.

Two opposing crescent-shaped magnets are secured on opposite sides of the inner tube 60 at the end 80. The magnets are spaced evenly, each extending over about one-fourth of the circumference of the inner tube 80. The magnets are preferably covered by a very thin layer of silicone or other material to prevent any interaction between the magnetic material and body chemistry. Preferably, the magnets are opaque to X-rays so that they may be guided by a fluoroscope.

Inside the inner tube 60 is the tool 24 which includes a cord or wire 86 extending through a flexible wall stiffener 88. At the bottom of the tool 24, the wall stiffening material has a larger diameter 90 for fitting within the reinforcing the enlarged area 62 of the inner tube. The elements 88, 90 may be thought of as a coiled spring made of plastic or other material. The wire 86 is marked with two color coded bands 120, 121 which aid the doctor who may not wish to use a fluoroscope. A combination of correlated sizes makes it possible for the doctor to tell if loop 28 and ring 36 are properly compressed inside the catheter 62 prior to removal of implant.

Inside the large area 90, tweezers 26 are secured to the bottom of the cord or wire 86. Preferably, when closed, these tweezers are substantially the same size as the inside diameter of section 90. They spring out under their own spring bias to open and become wider than this inside diameter of section 90 when they are pushed out of the end 90 of spring reinforcement 88. They close securely when they are pulled into the end 90. When the tweezers are extending from end 90 but still within catheter 80, the prongs are not open sufficiently to embrace loop 28. Therefore, additional width is needed to open the tweezers to the correct width while they are being extended past end 80. The slits 94, 96 allow the tweezers to open wider and thereby adjust the tweezers' width sufficiently to grasp loop.

As best seen in FIG. 6A, the bottom end of the inner tube 60 is slit at 94, 96 for a distance of about ¼ inch, up the side, slit 96 beginning after the end of the cord lumen. These slits are in the area between the semicircular magnets 82, 84. The slits are normally held closed by the resilience of the tube 60, unless the tweezer's prongs push out through them, thereby causing each slit to open approximately 2 mm before their covering becomes taut, preventing further opening. The tweezers' prongs may be positioned by aligning the oval handle 70 above the colored strips 69 on the handle of inner tube 60. When aligned, the prongs are in the correct position to grasp the loop 28 when the tweezers are extended. Therefore, the slits enable the tweezers' prongs to open wider than they otherwise could open inside the catheter 80 to reliably encircle the loop 28. Also, since the tweezers push outward, they will move stomach folds out of the tweezers' reach.

Since the spring bias of the tweezer's prongs opens them as they are pushed out of spring 90 and into the slits in the catheter, this procedure of opening the tweezers may be followed to release the loop 28 when the tube 32 is implanted. To remove the implanted tube, the tweezers are pushed out to open. The position of the tweezer's prongs may be manipulated by pulling cord 76 to curl the end of the inner tube 60 as it approachs the loop 28. The magnets 82, 84 attract the magnetic material in the loop 28, and the tweezer prongs assume the correct position for seizing the loop 28 as it is so attracted. To further assist in indexing the rotational position of the tweezers, the oval ring 70 may be turned to correspond with the location of stripes 69 printed on the inner tube handle.

In operation during implant removal, a connection is made between the catheter end 80 and the loop 28. The free end of loop 28 is drawn against the magnetic material 82, 84 on the end of the catheter 80. To check for a connection between the magnet and loop 28, move inner tube 60 up and down. If resistance is felt, the loop is connected to magnets. If so, position tweezer 26 and push it out of catheter 80 to grasp loop 28. Hold the disk 123 on wall reinforcement 88 against the inner tube handle. This causes section 90 to align with end 80 to close tweezers as they are pulled slightly into section 90. Pull up handle 70, bringing tweezers (loop 28 attached) into section 90. Ring 36 collapses behind loop into catheter 62. Ring 36 pushes section 90 upward as it is compressed into section 62. The ring and loop are compressed when green band 120 alignes with extending disk on wall reinforcement 88.

Prior to retrieval of the tube 32, the catheter is prepared for insertion down the patient's throat and into the stomach. A slow dissolving gelatin capsule 100

(FIG. 7) is placed in the end of inner tube 80 to streamline it and prevent it from snagging on the way down the throat. Once the catheter reaches the stomach, the handle 70 is pushed and the gelatin capsule is dislodged into the stomach where it slowly dissolves. The end of the catheter is then turned and tensioned by cord 76 to curl (FIG. 5) so that the magnets 82, 84 approach loop 28, the connection is seen in FIG. 1. The end of the implant in FIG. 2 may be prepared with a similar capsule device 100a for insertion into the alimentary track.

FIG. 8 shows a safety guard which may be used to secure the catheter parts for insertion into or removal from the patient's body. This safety guard comprises two spring loaded clamps 102, 104 rigidly secured together by a rod 106. Therefore, the clamp 102 may be attached around wire 86 and the clamp 104 may be attached around the inner tube 60. This means that there is no way for the tweezers 26 to inadvertently slip out of the large part 90 of the catheter during insertion or removal and the two tubes 20, 60 are telescoped together at a point in section 64. During implant, once the tube 32 is properly lodged in the intestine during insertion, the guard clamps 102, 104 are removed to manipulate catheter. During removal, the guard is attached after the stomach ring is securely captured in the large part 62 of the catheter. The length of the safety guard corresponds with the distance needed to compress the implant loop 28 and ring 36. The remainder of the tube 32 implant retains a compressed form when empty of food.

Two colored marks 120, 121 may be formed on the wire 86.

When handle 70 is pulled while the tweezers 26 have a grip upon loop 28, the ring 36 is captured and pulled into the catheter end 62 far enough so that mark 120 may be seen above the catheter top 123. However, if the tweezers do not have a grip upon loop 28, the handle 70 may be pulled further and the mark 121 will be seen above the catheter top 123. Conveniently, these marks 120, 121 may be color coded for easy identification.

Various modifications will occur to those who are skilled in the art. For example, the tweezers could be replaced by another form of tool. An electro-magnet 110 (FIG. 6B) could be enclosed in the catheter to hold or release a tab of magnetic material on the end of the tube. Also other means may be used for hooking or capturing the loop 28. Also, certain improvements may be made such as for example, cushioning the stomach ring 36 or altering support structure 34.

Those who are skilled in the art will readily perceive still other changes and modifications which may be made in the inventive structure. Therefore, the appended claims are to be construed broadly enough to cover all equivalent structures falling within the scope and the spirit of the invention.

I claim:

1. An instrument comprising an open-ended, thin-walled, balloon-like tube shaped to extend through at least a portion of an alimentary canal, the diameter and length of said tube being selected to treat an absorption-related disease, means for implanting said tube through a patient's mouth and throat, means for securing said tube entirely within the alimentary canal of an animal body for the purpose of passing digesting food solids and thereby treating absorption-related diseases, whereby a patient may consume whole food through the mouth, said whole food becoming partially digested in the stomach before coming into contact with said implanted instrument; and means for controlling a transfer of food chemicals from said digesting food solids through the walls of said implanted instrument to the alimentary canal by preventing or altering the transfer of said food chemicals between said implanted instrument and the walls of the alimentary canal.

2. The instrument of claim 1 and semi flexible means in said tube to provide an interrupted rigid mode of operation to facilitate insertion of said tube into said alimentary canal and a flexible mode of operation to enable said tube to be inserted without twisting.

3. The instrument of claim 1 and means for removably anchoring said tube in place inside a stomach so that said tube extends into but does not pass through said alimentary canal.

4. The instrument of claim 3 wherein said anchoring means comprises a ring having two distinct characteristics by which it has a rigid mode when said ring is pulled by the body in a direction which is away from the implanted position and a flexible mode for collapsing when said ring is pulled in the opposite direction to remove the implant, said anchor ring being attached to the end of said tube which may enter the body last during the implantation.

5. The instrument of claim 1 and means for inserting and removing said tube means into said alimentary canal via the throat, mating capture means on the ends of said tube and said inserting means which ends do not add any encumberances to the entrance and exit of food solids in said tube, said insertion means comprising a catheter having said capture means for capturing and holding said capture means on said tube while it is being inserted into or removed from said alimentary canal, and for releasing said tube after it is implanted, whereby said catheter may be removed while the implant is in place.

6. The instrument of claim 5 and slow dissolved means for streamlining the end of said catheter to enable insertion thereof without snagging, said slow dissolve means dissolving in the stomach or intestine when pushed out the end of said catheter.

7. The instrument of claim 5 wherein said capturing and holding means comprises an electro-magnet.

8. The instrument of claim 5 and slow dissolve means for streamlining the end of said tube to enable insertion thereof without snagging, said slow dissolve means dissolving in the stomach or intestine when pushed out the end of said catheter.

9. The instrument of claim 1 wherein the wall of the tube of said implanted instrument is flexible to have a small outer dimension when empty of said digesting food solids and to expand to a larger outer diameter when said digesting food solids pass through said tube, the wall of said implanted tube being proportioned for said food solids to be transported, responsive to peristaltic intestinal action.

10. The instrument of claim 1 wherein a multiplicity of holes are formed within the thin wall of said implanted tube to enable a transfer of food chemicals to take place, whereby intestinal tube secretions may enter said tube through said hles to further digest said food chemicals within said instrument, and said food chemicals within said instrument may leave said tube through said holes to be absorbed by the digestive tract.

11. The instrument of claim 1 wherein the thin walls of said implanted tube has a soft, crushable texture to enable digesting food solids to be transported through said implant by peristaltic means.

12. An instrument for controlling absorption through the walls of a passageway within an animal body, said instrument comprising an open-ended tube implant means having physical characteristics which fit entirely within the passageway and being shaped to extend through a selected portion of said body passageway, the walls of said tube means being impervious to chemicals of adjacent substances likely to be transported through said body passageway, said implant tube being open on both ends for enabling passage of said adjacent substance as it travels through said passageway, means comprising holes periodically piercing said tube for enabling the passage of controlled amounts of body fluids between the substance in said tube and said body passageway, semiflexible means in said tube to provide a rigid mode of operation to facilitate insertion of said tube into said body passageway and a flexible mode of operation to enable said tube to be inserted without twisting, said anchoring means comprises a semiflexible ring which has a rigid mode when pulled by the body in a direction which is away from the implanted position and a flexible mode for collapsing when pulled in the opposite direction to remove the implant, said anchor ring being attached to the end of said tube which may enter the body last during the implantation, means for inserting and removing said implant means in said body, said insert means comprising a catheter having means for capturing and holding said implant means while it is being inserted or removed and for releasing said implant means after it is implanted, said capturing and holding means being a pair of tweezers and said catheter including a confining portion into which said tweezers may be drawn to close and confine the said tweezers opening automatically when pushed out of said confining portion.

13. The instrument of claim 12 and magnet material on said implant means, magnetic means positioned on said catheter and near said tweezers for attracting said magnetic material, said tweezers, magnetic material, and magnetic means being aligned in mutually interrelated positions so that said tweezers grip and capture said magnetic means when said magnet attracts said magnetic material.

14. The instrument of claim 13 and means in said catheter near said tweezers for curling, guiding and directing the end of said catheter.

15. The instrument of claim 14 where said guiding and directing means comprises a series of semi-circumferential wedge slots cut therein, with a cord loosely running through the slots, said cord being attached to the distal end of said catheter, whereby said slots tend to close and the catheter tends to curl when said cord is pulled.

16. An instrument for controlling absorption through the walls of a passageway within an animal body, said instrument comprising an open-ended tube implant means having physical characteristics which fit entirely within the passageway shaped to extend through a selected portion of said body passageway, the walls of said tube means being impervious to chemicals of adjacent substances likely to be transported through said body passageway, means for inserting and removing said implant means in said body, said insert means comprising a catheter having means for capturing and holding said implant means while it is being inserted or removed and for releasing said implant means after it is implanted, whereby said catheter may be removed while the implant is in place, said catheter having three coaxial parts, a first of said three parts being a sheath for preventing irritation of the body when the inner parts are manipulated therein, other of parts including an inner tube and a flexible stiffening means with tool control means extending down the center of said coaxial parts, said tool being a pair of tweezers and said control means comprising means for pushing said tweezers out or pulling them into said catheter.

17. The instrument of claim 16 and safety means at the top of said catheter for preventing said tool from being accidentally pushed out of said catheter and for preventing said three parts from moving relative to each other.

18. A process for controlling the transfer of chemicals between foods in the intestine and body fluids, said process comprising:
 (a) implanting a thin-walled open-ended tube totally within the gastrointestinal tract for passing digesting food solids which are eaten by the person with the implant, said implant controlling the transfer of said chemicals between said solid food and the walls of said gastrointestinal tract, said implant being contained in its entirety within the gastrointestinal tract while it is implanted; and
 (b) using the implant while it is totally contained within said gastrointestinal tract for controlling an amount of such chemical transfer.

19. The process of claim 18 and the added step of restricting said transfer to cause weight loss.

20. The process of claim 18 and the added step of adding bulk to said implant for stimulating the squeezing peristal tic movements for extended periods of time during the passage of said food through said intestine to cause weight gain.

21. The process of transporting digesting food solids which are eaten in a normal manner by an animal, said food solids passing from the stomach through the animal's digestive tract, said process comprising the step of partially lining said gastrointestinal tract with a tube which is shaped and proportioned to fit against the interior of said gastrointestinal area, the walls of said tube being thin enough to transport food by normal peristaltic contractions of the animal's stomach and intestine and controlling chemical transfer between food solids while in said tube and said digestive tract, by forming a multiplicity of holes in said tube to enable controlled amounts of said food chemicals to escape from said tube through said holes and into the digestive tract.

22. The process of claim 21 wherein said digesting food solids are consumed in normal form, and not in digested or partially digested form, through the mouth of said animal having said digestive tract, said food becoming partially digested before coming into contract with said partially lined tract.

* * * * *

UNITED STATES PATENT AND TRADEMARK OFFICE
CERTIFICATE OF CORRECTION

PATENT NO. : 4,134,405
DATED : January 16, 1979
INVENTOR(S) : Julie A. Smit

It is certified that error appears in the above-identified patent and that said Letters Patent are hereby corrected as shown below:

Col. 4, line 27, after the period insert --Each of these four sections has a separate corresponding chain section since the non-flexible mode of the chain might otherwise prevent an adequate contouring, with these dimensions.--

Col. 7, line 61, change "the" to --and--

Col. 9, line 10, change "track" to --tract--

Col. 9, line 21, change "implant" to --implantation--

Col. 10, line 37, change "dissolved" to --dissolve--

Col. 10, line 61, change "hles" to --holes--

Signed and Sealed this

Twenty-sixth Day of June 1979

[SEAL]

Attest:

RUTH C. MASON
Attesting Officer

DONALD W. BANNER
Commissioner of Patents and Trademarks